(I)-2 wherein R indicates a hydrogen atom or a hydroxyl group. As the compound of this kind, 25-hydroxyvitamin $D_3$-26,23-peroxylactone and 1α,25-hydroxyvitamin $D_3$-26,23-peroxylactone may be mentioned. These compounds are novel compounds first found by the present inventors and they are compounds which have a γ-peroxylactone structure on the side chain. 25-hydroxyvitamin $D_3$-26,23-peroxylactone can be obtained according to the following procedures: by first giving vitamin $D_3$ or 25-hydroxyvitamin $D_3$ to rats, chickens, pigs, etc. in a toxicologically permissible dose after the ordinary method such as oral administration, intravenous injection, and intramuscular injection, and then extracting the desired compound from the serum collected from the blood of the rats, chickens, pigs, etc. about 3 to 10 days after the administration as a metabolite of the administered vitamin $D_3$ or 25-hydroxyvitamin $D_3$, and finally isolating on Sephadex LH-20 column chromatography or high pressure liquid chromatography.

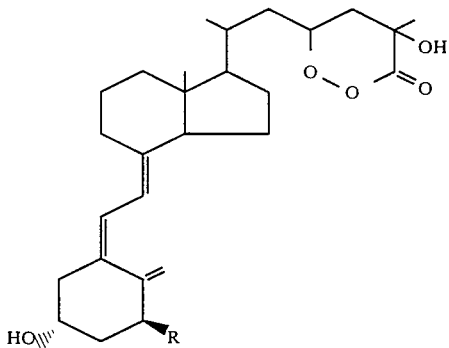

1α,25-dihydroxyvitamin $D_3$-26,23-peroxylactone can be obtained as a metabolite of 1α-hydroxyvitamin $D_3$ or 1α,25-dihydroxyvitamin $D_3$ according to the same method as the isolation and extraction of 25-hydroxyvitamin $D_3$-26,23-lactone.

Of these 25-hydroxyvitamin $D_3$-26,23-lactones, 25-hydroxyvitamin $D_3$-26,23-lactone and 1α,25-dihydroxyvitamin $D_3$-26,23-lactone are desirable from the viewpoint of pharmacological founctions and chemical stability, of which 1α,25-dihydroxyvitamin $D_3$-26,23-lactone is especially desirable. Of 1α,25-dihydroxyvitamin $D_3$-26,23-lactone, 23(S), 25(R)-1α,25-dihydroxyvitamin $D_3$-26,23-lactone, whose configuration around the carbon atoms at the 23- and 25-positions is the same as the natural type, is particularly desirable.

The aforementioned 25-hydroxyvitamin $D_3$-26,23-lactone and its derivatives have a function to control the calcium concentration in the serum of warm-blooded animals, especially a function to decrease the concentration of calcium in the serum of warm-blooded animals. Also 25-hydroxyvitamin $D_3$-26,23-lactone and its derivatives, of the present invention ensure high toxicological safety since it is a metabolite obtained in vivo from warm-blooded animals. Therefore, the present invention can be desirably applied to the treatment of diseases arising from the abnormally high concentration of calcium in the serum of warm-blooded animals. Also, in the case where a possible abnormal increase of calcium level in the serum of warm-blooded animals is foreseen, this invention can be used with the object of prevention before such abnormality takes place.

The present invention is appropriately applied to the treatment of diseases resulting from the high calcium levels in the serum, including, for instance, hypercalcemia due to the administration of 1α-hydroxyvitamin $D_3$, 1α,25-dihydroxyvitamin $D_3$, 1α,24-dihydroxyvitamin $D_3$, etc., hypercalcemia due to malignant tumor, hyperparathyroidism, and Behcet's disease etc.

The conditions to which the present invention is advisably applied include cases where vitamin D resistant patients who need the administration of vitamin $D_3$ in large doses and also patients with a malignant tumor who are afraid of having high calcium levels.

The present invention is originally designed to be fittingly applied to man; however, it also works usefully in the treatment of warm-blooded animals such as a pig, bovine, goat, sheep, horse, dog, cat, etc.

In the present invention, the aforementioned 25-hydroxyvitamin $D_3$-26,23-lactone and its derivatives are administered in a pharmaceutically effective amount such as 1 to 1000 ng/day/kg-body weight, desirably 5 to 200 ng/day/kg-body weight.

In the present invention, these 25-hydroxy-vitamin $D_3$-26,23-lactones can be administered once a day or several times, for instance, in two or three divided doses a day. The times of administration can be determined discretionarily in consideration of the conditions of diseased warm-blooded animals by a doctor in case of man and by a veterinarian or by a keeper under the direction of a veterinarian in case of warm-blooded animals other than man.

In the present invention, 25-hydroxyvitamin $D_3$-26,23-lactones can be administered to a living body via various routes. More particularly, 25-hydroxy-vitamin $D_3$-26,23-lactones can be administered either orally or parenterally, such as intramuscularly, intravenously, subcutaneously, or by way of a suppository, desirably orally. It is preferable to have these 25-hydroxyvitamin $D_3$-26,23-lactone and its derivatives administered in the form of a mixture combined with a pharmaceutically acceptable carrier. Thus the present invention offers a pharmaceutical composition for controlling the calcium concentration in the serum comprising 25-hydroxyvitamin $D_3$-26,23-lactone or its derivatives expressed by the aforementioned formula (I) and a pharmaceutically acceptable carrier. Since 25-hydroxyvitamin $D_3$-26,23-lactone and its derivatives have a specific pharmacological function to reduce the serum calcium levels, said pharmaceutical composition is very useful when used as a pharmaceutical composition to reduce the concentration of calcium in the serum.

As the pharmaceutically acceptable carrier, for instance, ethyl alcohol; such vegetable oils as corn oil, olive oil, cotton seed oil, coconut oil, almond oil, peanut oil, etc.; fish liver oil; oily esters such as Polysolvate 80 which is capable of making a pharmaceutical liquid composition; cacao butter, fatty acid triglyceride, etc. that are capable of making a pharmaceutical solid composition meltable at living body temperature; calcium carbonate, potato starch, alginic acid, lactose, etc. that are capable of making a pharmaceutical solid composition not meltable at living body temperature; and organic acid esters such as propylene glycol, polyethylene glycol, and ethyl oleate that make an aqueous or nonaqueous pharmaceutical solution or suspension composition may be mentioned.

The pharmaceutical composition of this invention may be made to contain such an antioxidant as ascorbic acid, butylated hydroxyanisole, and hydroquinone with

7α-ACYLTHIO-1α,2α-METHYLENE-3-OXO-17α-PREGN-4-ENE-21,17-CARBOLACTONES, THEIR PRODUCTION AND PHARMACEUTICAL PREPARATIONS CONTAINING THEM

BACKGROUND OF THE INVENTION

The present invention relates to new 7α-acylthio-1α,2α-methylene -3-oxo-17α-pregn-4-ene-21,17 carbolactones, processes for producing them and pharmaceutical preparations containing them as active ingredients.

In treatments with spironolactone there frequently occur undesirable endocrine side effects that are caused by the antiandrogenic and gestagenic activity of spironolactone. For example, the occurrence of gynecomastia is observed in extended treatment of male patients with spironolactone (Smith, W. G., The Lancet 1962, p 886; Mann, N. M., JAMA 1963, p 778; Clark, E., JAMA 1965, p 157; Greenblatt, D. J., JAMA 1973, p 82) as well as impotence (Greenblatt, D. J., JAMA 1973, p 82) which can be traced to the antiandrogenic side effect of this compound (Steelman, S. L. et al, Steroids 1963, p 449; Schane, H. P., J. of Clinical Endocrinology and Metabolism 1978, p 691).

The side effects on women treated with spironolactone, such as amenorrhea and menstrual irregularities, on the other hand, are ascribed to the gestagenic side effect of spironolactone. Both side effects can be demonstrated in animal experiments as well as in vitro using the conventional receptor binding test with the androgen or gestogen receptor.

SUMMARY OF THE INVENTION

Accordingly, it is an object of this invention to provide compounds that are superior to spironolactone in antialdosterone effect and at the same time exhibit endocrine side effects as low as possible and which are at worst comparable to those of spironolactone.

Upon further study of the specification and appended claims, further objects and advantages of this invention will become apparent to those skilled in the art.

These objects have been attained by providing 7α-acylthio-1α,2α-methylene -3-oxo-17α-pregn-4-ene-21,17-carbolactones of formula I

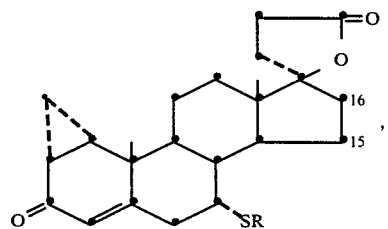

wherein

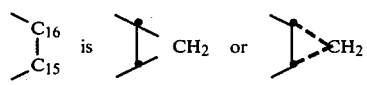

R is a lower saturated acyl radical of 2 to 4 carbon atoms.

DETAILED DISCUSSION

R in Formula I is a lower saturated acyl radical, e.g., $C_{2-4}$-alkanoyl, e.g., acetyl, propionyl or butryl, the acetyl and propionyl groups being preferred.

The new compounds of Formula I have the properties of neutralizing or reversing the effect of aldosterone or deoxycorticosterone on the elimination of sodium and potassium. The compounds according to this invention are thus suited for the treatment of certain forms of hypertension, e.g., those treatable by spironolactone, edemas, primary aldosteronism, and other endocrine disturbances caused by aldosterone. They can also be used as diuretics.

The antialdosterone effect of this invention was determined and measured in an experimental model by Hollmann (G. Hollmann et al, Tubular Effects and Renal Elimination of Spironolactones, Naunyn-Schmiedebergs Arch. Exp. Path Pharmak. 247 (1964), p 419; P. Marx, Renal Effects of d-aldosterone and Its Antagonist Spironolactone, Diss. Med. Fak. FU Berlin, 1966).

The androgen receptor binding test is conducted as follows:

The androgen receptor (protein) contained in the cytosol of a homogenate of rat prostates binds dihydrotestosterone (DHT) with high affinity but with low capacity. If this receptor is charged with $^3$H-DHT in the presence of the compound to be tested, the concentration and the binding affinity of the compound to be tested determine the degree to which $^3$H-DHT is displaced from the receptor. After separation of the receptor-bound DHT from the non-bound, binding can be determined in percent, and this value can be plotted against the logarithm of the molar concentration of the test substance. The concentration of the test substance required to displace the reference substance completely from the receptor is then determined. The competition factor (CF) as a measure of the binding strength is defined as the ratio of the concentration of the test substance to the concentration of the reference substance, so that a high CF value indicates low binding strength, whereas a low CF value indicates high affinity.

The antiandrogen effect can be determined with compounds which in themselves have no androgen effect but which through their high binding affinity fully or partially displace the body's own androgen from the receptor, as is observed to a certain degree with spironolactone. Thus, a high competition factor is desirable in the androgen and gestagen receptor tests.

The gestagen receptor test is conducted in analogous manner using cytosol from rat uterus homogenate.

The following table summarizes the relative values of the degree of antialdosterone effect (spironolactone=1) and the competition factors in the androgen receptor test ($K_A$) and in the gestagen receptor test ($K_G$) of spironolactone and the compounds of this invention as exemplified by 7α-acetylthio-1α,2α;15β,16β-dimethylene-3-oxo-17α-pregn-4-ene-21,17-carbolactone (B)
and
7α-acetylthio-1α,2α;15α,16α-dimethylene-3-oxo-17α-pregn-4-ene-21,17-carbolactone (C)

measured in the same way as the foregoing (i), (a). The results are shown in Table III. The data are expressed as the mean±S.E.M. Significantly different from control: a;p<0.001.

TABLE III

| Compound | | Intestinal Ca transport $^{45}$Ca serosal/ $^{45}$Ca mucosal | Serum Ca (mg/100 ml) |
|---|---|---|---|
| First dose | Second dose | | |
| Vehicle | Vehicle | 1.71 ± 0.13 | 4.84 ± 0.18 |
| 25-OH—D$_3$—26, 23-lactone | Vehicle | 1.80 ± 0.09 | 4.14 ± 0.19$^a$ |
| Vehicle | 1α,25-(OH)$_2$D$_3$ | 3.96 ± 0.18$^a$ | 5.82 ± 0.16$^a$ |
| 25-OH—D$_3$—26, 23-lactone | 1α,25-(OH)$_2$D$_3$ | 3.91 ± 0.10$^a$ | 4.88 ± 0.20 |

(b) Rats fed a low calcium vitamin D deficient diet for 6 weeks were divided into 4 groups of 5 rats. They received the first dose of 125 ng of 1α,25-(OH)$_2$D$_3$-26,23-lactone dissolved in 0.2 ml of 0.2% Triton X-100 solution or only vehicle intravenously. Twelve hours later, they received the second dose of 125 nm of 1α,25-(OH)$_2$D$_3$ dissolved in 0.2 ml of 0.2% Triton X-100 solution or only vehicle by the same route. Twelve hours after the second dose, the animals were killed and the intestinal calcium transport activity and the serum calcium concentration were measured in the same way as the aforementioned (i), (a). The results are shown in Table IV. The date are expressed as the mean±S.E.M. Significantly different from control: a;p<0.01 and b;p<0.001.

TABLE IV

| Compound | | Intestinal Ca transport $^{45}$Ca serosal/ $^{45}$Ca mucosal | Serum Ca (mg/100 ml) |
|---|---|---|---|
| First dose | Second dose | | |
| Vehicle | Vehicle | 1.66 ± 0.21 | 4.82 ± 0.09 |
| 1α,25-(OH)$_2$D$_3$—26, 23-lactone | Vehicle | 1.79 ± 0.13 | 4.12 ± 0.09$^b$ |
| Vehicle | 1α, 25-(OH)$_2$D$_3$ | 3.53 ± 0.14$^b$ | 5.94 ± 0.12$^b$ |
| 1α,25-(OH)$_2$D$_3$—26, 23-lactone | 1α, 25-(OH)$_2$D$_3$ | 3.62 ± 0.16$^b$ | 5.52 ± 0.12$^a$ |

It is apparent from Table III and Table IV that 1α,25-dihydroxyvitamin D$_3$ raises the calcium levels in the serum remarkably while contrastingly 25-hydroxyvitamin D$_3$-26,23-lactones of the present invention decrease the serum calcium levels remarkably.

Also it is clear that in case where 25-hydroxyvitamin D$_3$-26,23-lactone is administered (as the first dose) before 1α,25-dihydroxyvitamin D$_3$ is administered (as the second dose), the rise of the calcium levels in the serum due to 1α,25-dihydroxyvitamin D$_3$ is brought under control.

(iv) Increase of urinary calcium excretion by 1α,25-(OH)$_2$D$_3$-26,23-lactone

Male weanling rats of rht Wistar strain were fed a vitamin D deficient low calcium diet for 6 weeks. After the ligation of urethras, each of the five rats received an intravenous injection of 125 ng of 1α,25-(OH)$_2$D$_3$-26,23-lactone dissolved in 0.2 ml of 0.2% Triton X-100 solution or only vehicle. Twenty-four hours later, the rats were killed and urine was collected from their urinary bladders. The cencentration of calcium in the urine was determined by the OCPC (O-cresolphthalein complexone) method. the results are shown in Table V.

TABLE V

| Compound | Serum Ca (mg/100 ml) | Urinary Ca excretion (μg) |
|---|---|---|
| Vehicle | 4.90 ± 0.12 | 51.2 ± 3.6 |
| 1α,25-(OH)$_2$D$_3$—26,23-lactone | 3.97 ± 0.07$^b$ | 69.8 ± 4.8$^a$ |

The data are expressed as mean±S.E.M. Significantly different from control: a;p<0.05 and b;p<0.001.

It is clear from Table V that 1α,25-(OH)$_2$D$_3$-26,23-lactone of the present invention enhances the urinary calcium excretion.

EXAMPLE 2

Preparation of elastic capsules

1α,25-dihydroxyvitamin D$_3$-26,23-lactone was dissolved in fatty oil to obtain an oil solution of 7 μg/ml concentration. The shell components consisting of 100 parts by weight of gelatin, 20 parts by weight of glycerin, 0.2 part by weight of ethyl parahydroxybenzoate, 0.2 part by weight of propyl parahydroxybenzoate, 0.5 part by weight of 1-parasulfonylazo-2-naphthol-6-sulfonic acid disodium salt, and 80 parts by weight of purified water were melted by heating to prepare a shell making material. Elastic capsules, each containing 1 μg of 1α,25-dihydroxyvitamin D$_3$-26,23-lactone, were made with the use of thus prepared shell making material on a continuous elastic capsule making machine.

What we claim is:

1. A method to decrease the concentration of calcium in the serum of warm-blooded animals characterized by the administration of a pharmaceutically effective amount of 25-hydroxyvitamin D$_3$-26,23-lactones expressed by the following formula (I) to warm-blooded animals

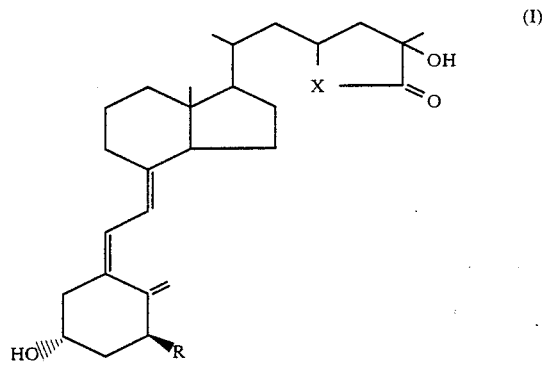

wherein R indicates a hydrogen atom or a hydroxyl group and X indicates —O— or —O—O—.

2. A method according to claim 1, wherein said 25-hydroxyvitamin D$_3$-26,23-lactones is 1α,25-dihydroxyvitamin D$_3$-26,23-lactone.

3. A method according to claim 1, wherein said pharmaceutically effective amount is 5 ng to 200 ng/kg—body weight/day.

4. A method according to any of claims 1, 2 or 3, wherein said warm-blooded animal is man.

5. A method according to claim 2, wherein said 25-hydroxyvitamin D$_3$-26,23-lactones is 23(S), 25(R)—1α,25-dihydroxyvitamin D$_3$-26,23-lactone.

6. A method according to claim 2, wherein said pharmaceutically effective amount is 5 ng to 200 ng/kg—body weight/day.

7. A method according to claim 5, wherein said pharmaceutically effective amount is 5 ng to 200 ng/kg—body weight/day.

* * * * * hour at room temperature and finally precipitated in ice water. The resulting precipitate is filtered off, rewashed with water, absorbed in $CH_2Cl_2$, dried with magnesium sulfate and concentrated in a vacuum. The resulting crude product is purified by column chromatography on silica gel. 5.5 g of 1α,2α;15β,16β-dimethylene-3-oxo-17α-pregna-4,6-diene-21,17-carbolactone is obtained.

UV: $\epsilon_{282}20\ 500$

Melting point: 203°–205° C.

(2a) 1α,2α;15α,16α-dimethylene-3-oxo-17α-pregna-4,6-diene-21,17-carbolactone 5.0 g of 15α,16α-methylene-3-oxo-17α-pregna-4,6-diene-21,17-carbolactone is stirred in 50 ml of dioxane with 5.0 g of 2,3-dichloro-5,6-dicyano-p-benzoquinone for 3 hours at 100° C. The reaction solution is cooled, the precipitated hydroquinone is suctioned off and rewashed with dioxane. The filtrate is thoroughly concentrated in a vacuum. The residue is absorbed in ether, washed with sodium bicarbonate solution and water, dried and evaporated. After chromatography on silica gel, 3.46 g of 15α,16α-methylene-3-oxo-17α-pregna-1,4,6-triene-21,17-carbolactone is obtained.

UV: $\epsilon_{222}=11\ 250$; $\epsilon_{254}=9\ 140$; $\epsilon_{299}=11\ 500$.

8.8 g of trimethylsulfoxonium iodide is stirred in 99 ml of dimethylsulfoxide with 1.391 g of sodium hydride, a 55% oil suspension, until the hydride dissolves. Then, 2.8 g of 15α,16α-methylene-3-oxo-17α-pregna-1,4,6-triene-21,17-carbolactone is added under argon and stirred again for 2 hours at room temperature. The reaction solution is stirred into ice water, made weakly acid with 2N sulfuric acid and the precipitate is filtered out. After dissolution in methylene chloride, it is washed with water, dried and evaporated. The residue is chromatographed on silica gel, and 2.1 g of 1α,2α;15α,16α-dimethylene-3-oxo-17-pregna-4,6-diene-21,17-carbolactone is obtained.

UV: $\epsilon_{281}=19\ 500$.

The starting compounds for (1a) and (2a) above are known and conventionally preparable (cf., e.g., U.S. Pat. No. 4,129,564).

EXAMPLE 1

2 ml of thioacetic acid is added dropwise to a solution of 4.7 g of 1α,2α;15β,16β-dimethylene-3-oxo-17α-4,6-diene-21,17-carbolactone in 15 ml of methanol at 60° C. and stirred for 5 hours at this temperature. After cooling, it is diluted with chloroform, washed with sodium bicarbonate and water, dried on magnesium sulfate and concentrated in a vacuum. The resulting crude product is purified by column chromatography on silica gel. 2.84 g of 7α-acetylthio-1α,2α;15β,16β-dimethylene-3-oxo-17α-pregna-4-ene-21,17-carbolactone is obtained.

UV: $\epsilon_{235}=16\ 000$

Melting point: 257°–259° C.

EXAMPLE 2

1.0 g of 1α,2α;15α,16α-dimethylene-3-oxo-17α-pregna-4,6-diene-21,17-carbolactone is stirred in 20 ml of methanol with 4 ml of water and 1.5 ml of thioacetic acid for 16 hours at room temperature. The reaction solution is then diluted with ether, washed with sodium bicarbonate solution and water, dried and evaporated. The residue is chromatographed on silica gel and, after diisopropyl ether trituration, 460 mg of 7α-acetylthio-1α,2α;15α,16α-dimethylene-3-oxo-17α-pregna-4-ene-21,17-carbolactone with a melting point of 246° C. is obtained.

UV: $\epsilon_{234}=15\ 600$.

From the foregoing description, one skilled in the art can easily ascertain the essential characteristics of this invention, and without departing from the spirit and scope thereof, can make various changes and modifications of the invention to adapt it to various usages and conditions.

What is claimed is:

1. A 7α-acylthio-1α,2α-methylene-3-oxo-17α-pregn-4-ene-21,17-carbolactone of the formula

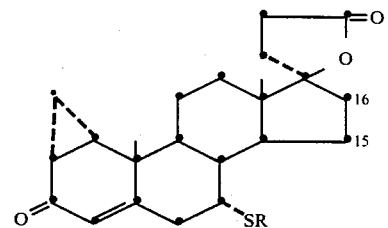

wherein

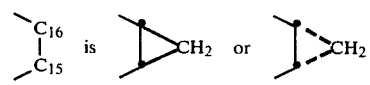

and

R is $C_{2-4}$-alkanoyl.

2. 7α-acetylthio-1α,2α;15β,16β-dimethylene-3-oxo-17α-pregn-4-ene-21,17-carbolactone, a compound of claim 1.

3. 7α-acetylthio-1α,2α;15β,16β-dimethylene-3-oxo-17α-pregn-4-ene-21,17-carbolactone, a compound of claim 1.

4. A compound of claim 1 wherein

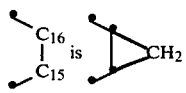

5. A compound of claim 1 wherein

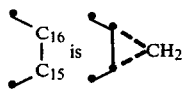

6. A compound of claim 1 wherein R is acetyl.

7. A compound of claim 1 wherein R is propionyl.

8. A compound of claim 1 wherein R is butyryl.

9. A pharmaceutical composition comprising an antialdosterone effective amount of a compound of claim 1 and a pharmaceutically acceptable carrier.

10. A pharmaceutical composition of claim 9 wherein the amount of antialdosterone compound is 10–100 mg.

11. A method of achieving an antialdosterone effect in a patient in need of such treatment comprising administering to the patient an amount of a compound of claim 1 effective as an antialdosterone agent.

12. A method of claim 11 wherein the amount of antialdosterone compound administered is 20–500 mg per day.

13. A method of claim 10 wherein the administration is oral.

* * * * *